United States Patent
Imran

[11] Patent Number: 5,906,631
[45] Date of Patent: May 25, 1999

[54] METHOD AND DEVICE FOR SEALING VASCULAR PUNCTURE WOUNDS

[75] Inventor: Mir A. Imran, Los Altos Hills, Calif.

[73] Assignee: Surface Genesis, Inc., Menlo Park, Calif.

[21] Appl. No.: 08/985,952

[22] Filed: Dec. 5, 1997

[51] Int. Cl.$^6$ .................................................. A61B 17/08
[52] U.S. Cl. ............................................................ 606/213
[58] Field of Search .................................. 606/213, 215, 606/216, 151, 139, 144, 148, 146; 604/96, 98, 181; 128/898

[56] References Cited

U.S. PATENT DOCUMENTS

| | | | |
|---|---|---|---|
| 4,727,730 | 3/1988 | Boiarski et al. | 606/213 |
| 4,929,246 | 5/1990 | Sinofsky . | |
| 5,061,274 | 10/1991 | Kensey . | |
| 5,192,300 | 3/1993 | Fowler . | |
| 5,326,350 | 7/1994 | Li | 623/11 |
| 5,376,120 | 12/1994 | Sarver et al. | 623/16 |
| 5,391,183 | 2/1995 | Janzen et al. | 606/213 |
| 5,443,481 | 8/1995 | Lee . | |
| 5,486,195 | 1/1996 | Myers et al. . | |
| 5,496,332 | 3/1996 | Sierra et al. | 606/139 |
| 5,529,577 | 6/1996 | Hammerslag . | |
| 5,653,730 | 8/1997 | Hammerslag | 606/214 |
| 5,766,206 | 6/1998 | Wijkamp et al. | 606/213 |

OTHER PUBLICATIONS

Datascope introduces VasoSeal International and US patents pending copyright 1991 Datascope Corp.

*Primary Examiner*—Michael Buiz
*Assistant Examiner*—Vikki Trinh
*Attorney, Agent, or Firm*—Flehr Hohbach Test Albritton and Herbert

[57] ABSTRACT

Method and device for sealing puncture wounds in a vascular walls wherein a cylinder of compliant material with a coating of hydrophilic material is placed with one end of the cylinder against the side wall of a vessel. Axial pressure is then applied to the other end of the cylinder to deform the cylinder and flatten it into a disk which increases in lateral dimension and becomes embedded in tissue over the wound. The hydrophilic material expands on the disk to seal the wound. A clot promoter in the coating reverses the effects of heparin and accelerates clot formation.

23 Claims, 2 Drawing Sheets

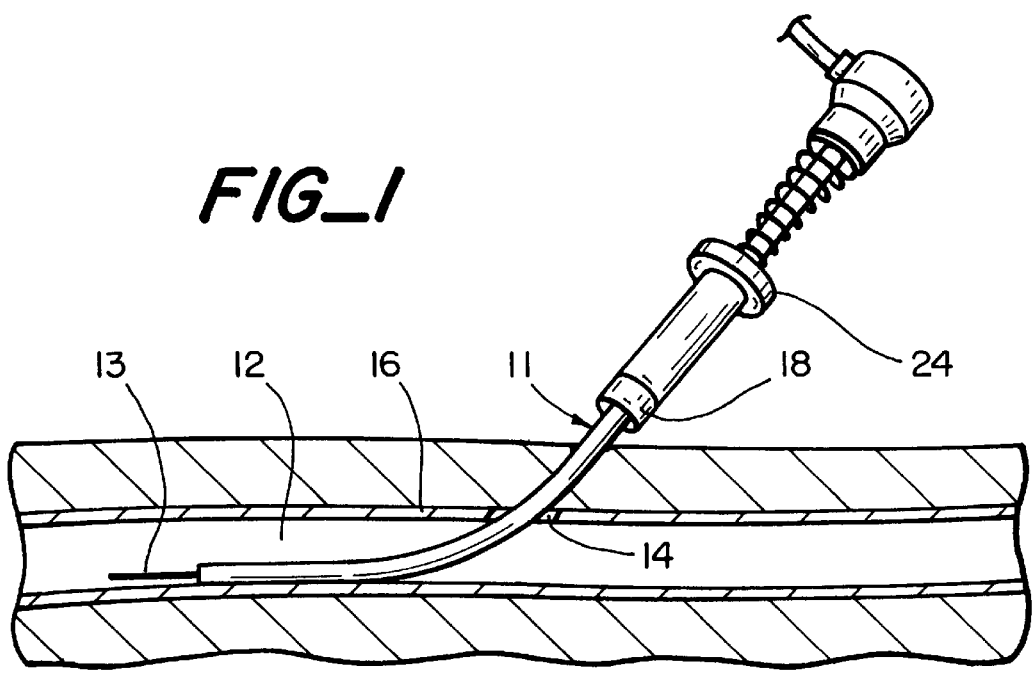
FIG_1
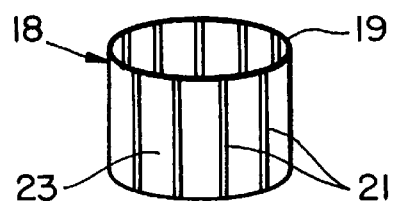
FIG_2
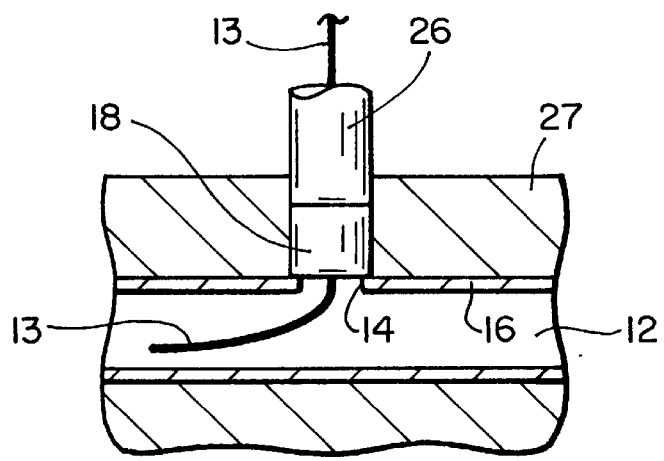
FIG_3

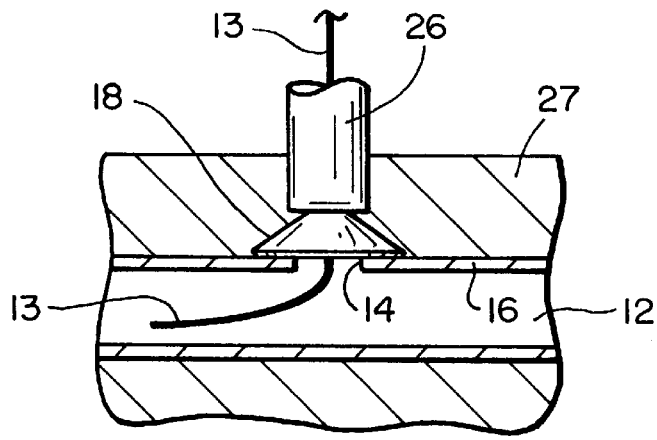
FIG_4
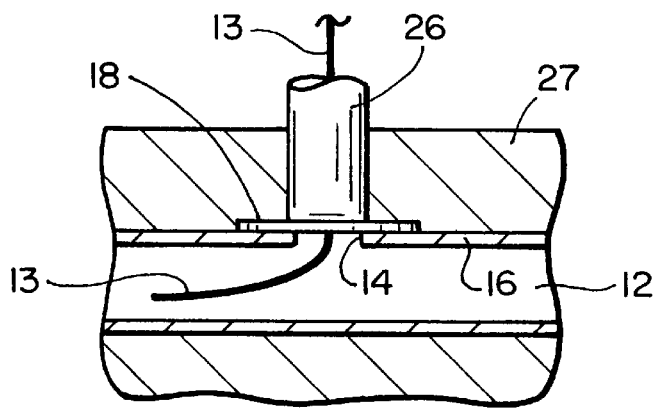
FIG_5
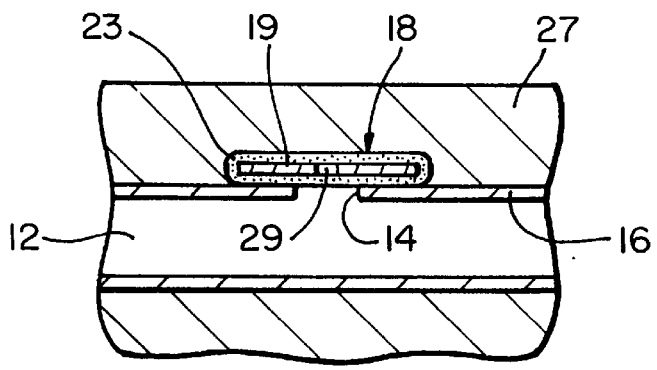
FIG_6

METHOD AND DEVICE FOR SEALING VASCULAR PUNCTURE WOUNDS

This invention pertains generally to medical devices and methods and, more particularly, to a method and device for sealing puncture wounds produced in the walls of blood vessels during vascular access procedures.

Vascular punctures are made routinely for various types of vascular procedures both in the coronaries and in the peripherals. Such procedures include angiographic examination, angioplasty, atherectomy, stent deployment, electrophysiological procedures, and various other measurement and treatment procedures. All of these procedures are conducted through the vascular system, mostly through the arteries but sometimes through the veins. In all such procedures, the opening through which the catheter or sheath is introduced must be closed and sealed as quickly as possible once the procedure is completed.

The most common method of sealing the wound is the application of pressure over the puncture site to stagnate the blood and cause it to clot. This typically takes a minimum of ½ hour, but it can take substantially longer. Thereafter, the patient must remain immobilized for a period of time and is kept in the hospital for observation for up to 24 hours because of the possibility that the clot will be dislodged.

Another problem with this approach is that the clotting process is slowed down by heparin which is often given to patients to prevent the formation of clots during the procedure. Depending upon the patient's metabolism and the amount of heparin given to him, it may take longer for the anti-clotting agent to wash out of the patient's system or be metabolized. This can increase the time required for the clot to form, thereby increasing the chances of complications and requiring a longer period of observation.

Heretofore, there have been some attempts to produce faster closing of the puncture site. In one such technique, the wound is closed by sutures placed in the vessel wall by needles which are inserted into and withdrawn from the vessel. This technique has a success rate of only about 80 to 85 percent. The sutures are not always placed in the optimum position, in which case the wound continues to leak and requires continued compression until clotting occurs. Also, if one or more of the needles is only partially deployed and cannot be retracted, it must be removed surgically, which can lead to major complications.

Another technique heretofore employed involves the use of a collagen plug which is placed over the vessel to prevent bleeding. Here again, the success rate is only about 80 percent. In the other 20 percent of the cases, the plug is not properly deployed or comes off, especially with patients who are thin and have relatively small veins or arteries.

A related technique involves the use of a collagen plug with an anchor which goes inside the vessel. The success rate with this technique is once again only about 80 to 85 percent in the hands of a skilled physician. These devices are relatively expensive, and they require the use of a separate device for delivery, In addition, there is a chance of embolization of the anchoring device which is also made of collagen.

Because of such problems, prior attempts to provide faster sealing of vascular punctures have not found very wide acceptance. They are currently used in only about one percent of the cases, with compression still being used in the vast majority of them.

It is in general an object of the invention to provide a new and improved method and device for sealing puncture wounds produced in the walls of blood vessels during vascular access procedures.

Another object of the invention is to provide a method and device of the above character which overcome the limitations and disadvantages of techniques heretofore employed.

These and other objects are achieved in accordance with the invention by forming a cylinder of compliant material with a coating of hydrophilic material, placing one end of the cylinder against the side wall of a vessel, pushing on the other end of the cylinder to deform the cylinder and flatten it into a disk which increases in lateral dimension and becomes embedded in tissue over the wound, and expanding the hydrophilic material to seal the wound. A clot promoter in the coating reverses the effects of heparin and accelerates clot formation.

FIG. 1 is an isometric view of a medical instrument with one embodiment of a closure device incorporating the invention.

FIG. 2 is an enlarged isometric view of the closure device in the embodiment of FIG. 1.

FIGS. 3–6 are cross-sectional views illustrating the operation and use of the closure device in the embodiment of FIG. 1.

In FIG. 1, the invention is illustrated in conjunction with an introducer sheath 11 through which catheters and other devices can be introduced into the vascular system of a patient. The sheath is inserted into a vessel 12 over a guide wire 13 and through a puncture 14 in the wall 16 of the vessel.

A closure device 18 is slidably mounted on the introducer sheath. This device comprises a cylinder having a very thin side wall 19 fabricated of a compliant bioabsorbable material such as polylactic acid (PLA). A plurality of circumferentially spaced ribs 21 extend longitudinally of the side wall. These ribs are fabricated of a less compliant material than the portions of the wall between them, such as PLA of greater hardness or higher durometer. PLA is a particularly preferred material for use in this device because it is not only readily deformable, but it also gets resorbed in the body very quickly without causing inflammation or other undesirable side effects.

A coating 23 of hydrophilic material in the form of a hydrogel such as an acrylamide gel is applied to the cylinder. The coating also includes a clot promoter such as protamine sulphate or calcium hydroxide which is mixed into the hydrogel to reverse the effects of heparin and accelerate clot formation. The coating is applied to both surfaces of the cylinder, then dried in a vacuum drying chamber so that it will be dry and not tacky in use.

An actuator 24 is slidably mounted on the sheath on the proximal side of the closure device for advancing the device along the sheath toward the outer wall of the vessel. During the procedure for which the puncture is formed, the closure device and the actuator remain outside the body. When the procedure is completed and the sheath is being withdrawn, the closure device is advanced along the sheath with the actuator until the distal end of the cylinder engages the outer wall of the vessel. Once the closure device has been positioned against the vessel, the actuator is withdrawn with the remainder of the sheath, leaving the guide wire and the closure device in place.

After the sheath is withdrawn, a tool 26 is inserted along the guide wire for flattening the cylinder into a disk. As illustrated in FIGS. 3–5, the tool is brought into engagement with the proximal end of the cylinder and pushed toward the wall of the vessel. Continued pressure on the tool causes the compliant side wall of the cylinder to deform in a conical fashion, with the distal portion of the cylinder flaring out and the proximal portion flaring in. As the wall is flattened, it increases in lateral dimension and becomes embedded in the tissue 27 over the puncture. The relatively stiff ribs maintain structural integrity and facilitate deformation of the cylinder wall in the desired manner as it is pressed against the vessel. The ribs also help to prevent the wall from simply collapsing when the axial pressure is applied as it might otherwise do if it were too soft or compliant.

The dimensions of the cylinder are such that a small opening 29 is left in the center of the disk when the wall is completely flattened. This opening is slightly larger than the guide wire 13 which passes through it. The flattened disk preferably has a diameter on the order of twice the diameter of the puncture site, and this relationship is obtained by making the length and the diameter of the cylinder substantially equal in dimension. Thus, for example, with an 8 French introducer in which the outer diameter of the sheath is on the order of 3 mm, the cylinder would have an inside diameter of about 3 mm, a wall thickness on the order of 0.010–0.015 inch (0.254–0.381 mm), and an outside diameter and length on the order of 3.5 or 3.6 mm. Once the cylinder has been flattened, the guide wire is removed.

As the hydrogel coating absorbs moisture from the blood, it expands, closing the opening in the disk and sealing the wound. As illustrated in FIG. 6, the expansion is such that the disk approximately triples in thickness, filling in any cracks or crevices which might otherwise permit leakage.

Any blood which does start to leak around or through the device comes into contact with the clot promoting compound in the coating. This causes the effects of any heparin in the blood to be reversed locally and promotes rapid clot formation around the device.

The invention has a number of important features and advantages. It provides quick and effective sealing of puncture wounds in vascular walls. The device digs into the tissue above the wound as it is flattened, thereby holding the device securely in place and preventing it from sliding out of position or popping out. With the hydrogel coating, the device is self-sealing, and the clot promoter in the coating provides local reversal of heparin effects and assures rapid clot formation. With the invention, a clot is typically formed in a minute, or so, and the patient can move about and walk without fear of leakage. The device can be manufactured very inexpensively and since it is integrated into the introducer, it does not require hospitals to stock another separate device for closing the wounds.

It is apparent from the foregoing that a new and improved method and device for sealing puncture wounds in vascular walls have been provided. While only certain presently preferred embodiments have been described in detail, as will be apparent to those familiar with the art, certain changes and modifications can be made without departing from the scope of the invention as defined by the following claims.

I claim:

1. A device for use in sealing a puncture wound in a vascular wall, comprising a hollow cylinder of compliant material which flattens into a disk that increases in lateral dimension and becomes embedded in tissue over a wound when one end of the cylinder is pressed against the wall of a vessel around the wound, and a coating of hydrophilic material on the cylinder which expands to seal the wound.

2. The device of claim 1 wherein the cylinder is fabricated of polylactic acid.

3. The device of claim 1 wherein the hydrophilic material is an acrylamide gel.

4. The device of claim 1 wherein the coating on the cylinder also includes a clot promoter.

5. The device of claim 4 wherein the clot promoter is selected from the group consisting of protamine sulphate, calcium hydroxide, and combinations thereof.

6. The device of claim 1 wherein the cylinder includes a thin side wall and a plurality of circumferentially spaced, longitudinally extending ribs on the side wall.

7. The device of claim 6 wherein the ribs are fabricated of a less compliant material than the side wall.

8. The device of claim 1 wherein the cylinder has a length and a diameter such that a central hole of greater diameter than a guide wire is left in the disk when the cylinder is flattened.

9. The device of claim 8 wherein the length of the cylinder is substantially equal to the diameter.

10. A method for sealing a puncture wound in a vascular wall comprising the steps of placing one end of a hollow cylinder of compliant material against the side wall of a vessel, pushing on the other end of the cylinder to deform the cylinder and flatten it into a disk which increases in lateral dimension and becomes embedded in tissue over the wound, and expanding a coating of hydrophilic material on the cylinder to seal the wound.

11. The method of claim 10 wherein the cylinder is placed against the vascular wall over a sheath which is removed before the cylinder is flattened.

12. The method of claim 10 wherein the cylinder is placed against the vascular wall over a guide wire, and the dimensions of the cylinder are such that a central hole is formed in the disk about the guide wire.

13. The method of claim 12 wherein the hole in the disk is sealed by the expanding hydrophilic material when the guide wire is removed.

14. A medical device comprising an introducer sheath adapted to be inserted into a vessel through a puncture in a wall of the vessel, a hollow cylinder of compliant material slidably mounted on the sheath, means for advancing the cylinder along the sheath to bring the distal end of the cylinder into engagement with the wall of the vessel, and means operable upon withdrawal of the sheath for pushing against the proximal end of the cylinder to flatten the cylinder into a disk that increases in lateral dimension and becomes embedded in tissue over the puncture.

15. The medical device of claim 14 wherein the cylinder is fabricated of polylactic acid.

16. The medical device of claim 14 including a coating of hydrophilic material on the cylinder which expands to seal the puncture when the disk is embedded in the tissue.

17. The medical device of claim 16 wherein the hydrophilic material is an acrylamide gel.

18. The medical device of claim 16 wherein the coating on the cylinder also includes a clot promoter.

19. The medical device of claim 18 wherein the clot promoter is selected from the group consisting of protamine sulphate, calcium hydroxide, and combinations thereof.

20. The device of claim 14 wherein the cylinder includes a thin side wall and a plurality of circumferentially spaced, longitudinally extending ribs on the side wall.

21. The device of claim 20 wherein the ribs are fabricated of a less compliant material than the side wall.

22. The device of claim 14 wherein the cylinder has a length and a diameter such that a central hole of greater diameter than a guide wire is left in the disk when the cylinder is flattened.

23. The device of claim 22 wherein the length of the cylinder is substantially equal to the diameter.

* * * * *